Figure 1:
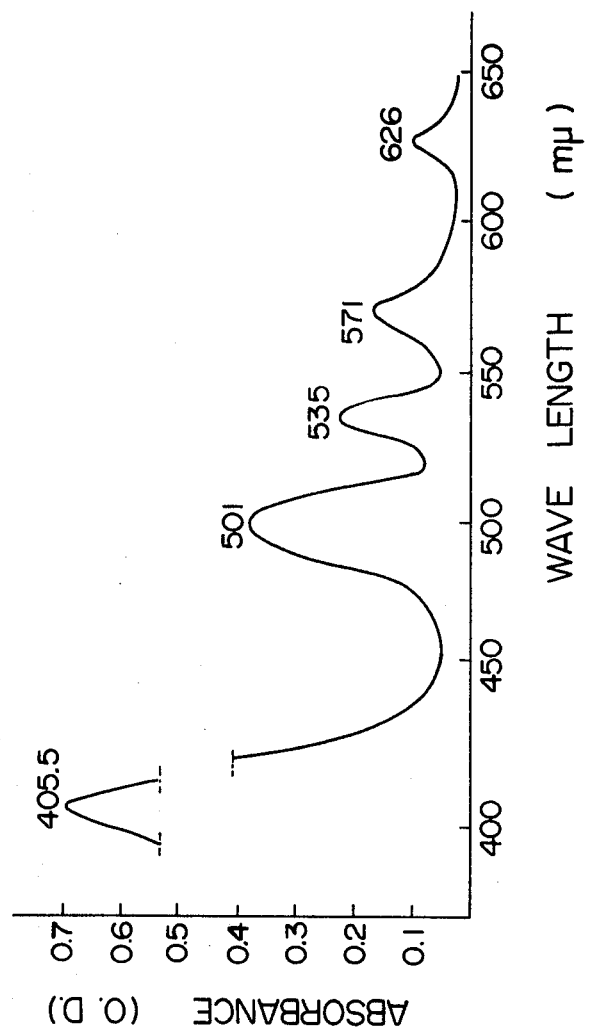

| United States Patent [19] | [11] | 4,370,415 |
|---|---|---|
| Kojima et al. | [45] | Jan. 25, 1983 |

[54] PROCESS FOR PRODUCING UROPORPHYRIN III

[75] Inventors: Ichiro Kojima, Yokosuka; Kenji Maruhashi, Yokohama; Yasuo Fujiwara, Tokyo, all of Japan

[73] Assignee: Nippon Oil Company, Ltd., Tokyo, Japan

[21] Appl. No.: 204,789

[22] Filed: Nov. 7, 1980

[30] Foreign Application Priority Data

Nov. 7, 1979 [JP] Japan .................................. 54-143198

[51] Int. Cl.³ .............................................. C12P 17/18
[52] U.S. Cl. ..................................... 435/119; 435/830
[58] Field of Search ................................. 435/118, 119

[56] References Cited

U.S. PATENT DOCUMENTS 3,902,967  9/1975  Chibata et al. ...................... 435/172
4,115,197  9/1978  Queener .............................. 435/172

OTHER PUBLICATIONS

Biochemical Journal, vol. 62, pp. 78–93 (1956).
Hoppe–Seyler's Zeitschrift for Physiological Chemistry, vol. 354(8), p. 841 (1973).

*Primary Examiner*—Lionel M. Shapiro
*Attorney, Agent, or Firm*—Wenderoth, Lind & Ponack

[57] ABSTRACT

A process for producing uroporphyrin III, which comprises cultivating a uroporphyrin III-producing microorganism of the genus Arthrobacter in a culture medium containing a carbon source, a nitrogen source and a mineral, and recovering uroporphyrin III from the culture broth.

7 Claims, 3 Drawing Figures

PROCESS FOR PRODUCING UROPORPHYRIN III

This invention relates to a process for producing uroporphyrin III, and particularly, to a process for producing a known substance, uroporphyrin III, having a porphyrin structure which has extensive applications as medicines, intermediates for synthesis of medicines, intermediates for production of vitamin $B_{12}$ and red dyes for foods and drinks in high yields at low cost by an industrially easy operation by utilizing a microorganism of the genus Arthrobacter which has not been known previously to produce uroporphyrin.

More specifically, this invention relates to a process for producing uroporphyrin III, which comprises cultivating a uroporphyrin III-producing microorganism of the genus Arthrobacter in a culture medium containing a carbon source, a nitrogen source and a mineral, and recovering uroporphyrin III from the culture broth.

The uroporphyrin III is a known substance having the following formula.

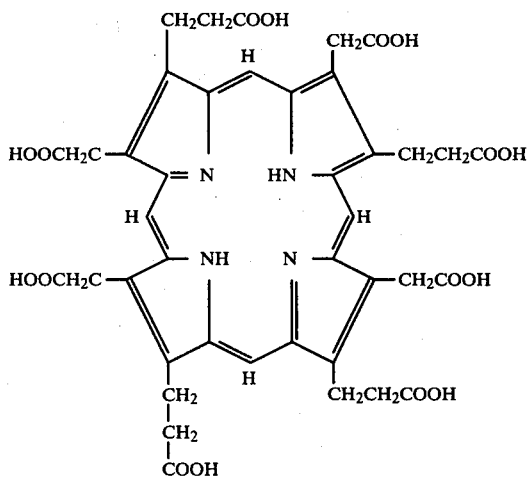

It has previously been known that microorganisms belonging to the genus Rhodopseudomonas such as *Rhodopseudomonas spheroides* and microorganisms belonging to the genus Propionibacterium such as *Propionibaceterium granulosum* and *Propionibacterium acnes* have the ability to produce uroporphyrin III. However, microorganisms of the genus Arthrobacter have never been known to produce uroporphyrin III.

Biochem, J., 62, page 78, 1956 which specifically describes the amount of uroporphyrin III produced gives 4 mg/liter of culture broth as the maximum amount of uroporphyrin III produced in a submerged culture using *Rhodopseudomonas spheroides*. Such a method can scarcely be utilized for industrial production of uroporphyrin III.

The present inventors have worked extensively on a process for producing uroporphyrin III in high and commercially feasible yields even by submerged fermentation.

Their work has led to the new discovery that microorganisms of the genus Arthrobacter produce uroporphyrin III. It has also been found that the uroporphyrin III-producing microorganisms of the genus Arthrobacter produce uroporphyrin III in an amount of, say, about 100 mg/liter of culture broth which amounts to about 25 times the maximum amount (4 mg/liter of culture broth) which a microorganism of the genus Rhodopseudomonas or Propionibaceterium can produce.

They have also found that the amount of uroporphyrin III to be produced can be markedly increased by using varieties or mutants of uroporphyrin III-producing strains of the genus Arthrobacter which have a greater ability to produce uroporphyrin III, cultivating the microorganisms in a culture medium containing L-cystine and/or $Mg^{++}$, or by suitable combinations of these conditions.

It is an object of this invention therefore to provide a process for producing uroporphyrin III in high yields at low costs by an industrially easy operation, which comprises utilizing a uroporphyrin III-producing microorganism of the genus Arthrobacter which has not been known previously to have the ability to produce uroporphyrin III.

The above and other objects and advantages of this invention will become more apparent from the following description.

Examples of the uroporphyrin III-producing microorganism of the genus Arthrobacter which is used in the process of this invention are *Arthrobacter hyalinus*, *Arthrobacter pascens*, and their varieties or mutants.

*Arthrobacter hyalinus* is a known freely-accessible strain deposited as FERM-P No. 3125 in Fermentation Research Institute (FRI), Agency of Industrial Science and Technology, Japan; as ATCC 31263 in American Type Culture Collection; and as DSM 867 in German Collection of Microorganisms. The microbiological properties of this strain are described, for example, in Japanese Laid-Open Patent Publication No. 94498/77. 5-Methyl-DL-tryptophan-resistant strain NOC11001, a mutant of *Arthrobacter hyalinus*, is deposited as FERM-P No. 5256 in FRI, Japan, as ATCC No. 31736 in American Type Culture Collection, and as DSM 1932 in German Collection of Microorganisms. Coproporphyrin III-resistant strain NOC11002, a mutant of *Arthrobacter hyalinus*, is deposited as FERM-P No. 5259 in FRI, Japan as ATCC No. 31739 in American Type Culture Collection, and as DSM 1933 in German Collection of Microorganisms.

*Arthrobacter pascens* is a known freely-accessible strain deposited as IFO 12139 in Institute for Fermentation, Osaka, Japan, and as ATCC 13346 in American Type Culture Collection. The microbiological properties of this strain are described, for example, in Bergey's Manual of Determinative Bacteriology, 8th edition. L-tryptophan-resistant strain NOC11003, a mutant of *Arthrobacter pascens*, is deposited as FERM-P No. 5257 in FRI, Japan as ATCC No. 31737 in American Type Culture Collection, and as DSM 1934 in German Collection of Microorganisms.

The above varieties of mutants differ from the parent strains only in that their ability to produce uroporphyrin III is improved over that of the parent strain. Their microbiological properties are substantially the same as those of the parent strains, and they can be easily obtained from the aforesaid known and freely accessible parent strains by methods known to those skilled in the art. For example, such varieties or mutants can be obtained from known mutation treating means such as ultraviolet irradiation or irradiation of $Co^{60}$ isotope. In one embodiment, a parent strain is subjected to the aforesaid irradiation treatment, and the treated strain is cultivated in a mineral-agar medium containing an agent for inhibiting the production of uroporphyrin III. If desired, the above irradiating treatment and fermentation cultivation are repeated, and a strain having an increased ability to produce uroporphyrin III can be recovered. The above cultivation can be performed under the same cultivation conditions as those set for cultivating the parent strain. Examples of the inhibiting agent include uroporphyrin III, coproporphyrin III, L-tryptophan, 5-methyl-DL-tryptophan, and other known inhibitors.

Accordingly, the present invention can also provide a process for producing a variety or mutant of a uroporphyrin III-producing microorganism, which comprises subjecting a uroporphyrin III-producing microorganism belonging to the genus Arthrobacter to irradiation, cultivating the treated microorganism in a culture medium containing an agent for inhibiting the production of uroporphyrin III, and recovering a strain having an increased ability to produce uroporphyrin III from the culture broth.

According to this invention, uroporphyrin III can be produced by cultivating the uroporphyrin III-producing microorganism of the genus Arthrobacter in a culture medium, and recovering uroporphyrin III directly or indirectly from the culture broth. The amount of uroporphyrin III produced can be often increased further by utilizing a culture medium containing L-cystine, or $Mg^{++}$, or both.

In the practice of the process of the present invention, a culture medium containing a carbon source, a nitrogen source, a mineral source, etc. can be used as the aforesaid medium. This culture medium may further contain L-cystine, $Mg^{++}$, an antifoamer or other components.

Examples of the carbon source are carbohydrates, alcohols, hydrocarbons and bran. Examples of the nitrogen source are corn steep liquor, yeast extract, meat extract, peptone, fish meal, ammonium salts, nitrate salts and urea. The mineral source includes inorganic salts such as phosphates, magnesium salts, zinc salts, calcium salts, manganese salts, molybdenum salts and copper salts.

The composition of the culture medium can be changed as desired, and during the fermentation, these carbon, nitrogen and mineral sources may be additionally supplied. For example, when an alcohol is used as the carbon source, the amount of uroporphyrin III produced can be increased by adding the alcohol when the concentration of the residual alcohol is low, or before, during or after the starting of production of uroporphyrin III. Preferably, an iron salt is substantially absent in the culture medium during the cultivation.

The cultivation is carried out under aerobic conditions by shaking or stirring. Preferably, it is preferred to pass the air at a relatively low rate. In other words, it is preferred to adjust the supply rate of air to a low level during the cultivation so that the amount of dissolved oxygen in the culture medium is maintained at a low level.

The cultivation temperature is, for example, about 20° C. to about 40° C., and the pH of the culture medium is about 4 to about 9.5. The suitable cultivation time is usually about 2 to about 30 days, and may be changed properly depending upon the selection of other cultivating conditions.

The amount of uroporphyrin III produced can often be increased by including L-cystine and/or $Mg^{++}$ in the culture medium. Various water-soluble magnesium compounds can be utilized as compounds giving $Mg^{++}$. Specific examples are magnesium sulfate, magnesium chloride, magnesium nitrate, magnesium acetate, and other magnesium compounds. The amount of L-cystine and/or $Mg^{++}$ can be properly selected. For example, the amount of L-cystine is about 0.1 g to about 5 g per liter of the culture medium, and the amount of $Mg^{++}$ is about 0.5 g to about 10 g per liter of the culture medium.

Uroporphyrin III builds up in the culture broth in an amount markedly increased over the case of using known uroporphyrin III-producing microorganisms. Uroporphyrin III can be recovered from the culture broth by various means.

For example, uroporphyrin III can be recovered from the culture both in good yields by using acetic acid-acidified ethyl acetate and other suitable ester extracting agents. In extraction, it is the common practice to extract the culture broth after microbial cells and other solid components have been separated from it. Furthermore, it is possible to obtain a uroporphyryrin concentrate by adjusting the pH of the culture broth freed from the microbial cells and other solid components to about 1.6 to 3.6 to precipitate uroporphyrin III isoelectrically, and subjecting the precipitate to a suitable solid-liquid separating means such as filtration or centrifugal separation.

The uroporphyrin III may be recovered in the form of a methyl ester by treating the concentrate or extract obtained in the above manner with, for example, HCl-methanol to convert uroporphyrin III to its methyl ester, and optionally purifying the methyl ester by a chromatographic technique using alumina. Or uroporphyrin III may be recovered by treating the resulting concentrate or extract by liquid chromatography, for example, high-performance liquid chromatography on a column of a styrene-divinylbenzene gel. When uroporphyrin III is recovered in the form of an ester, it may optionally be converted to its salt by hydrolysis. For example, this can be performed by dissolving the uroporphyrin III ester in an organic solvent such as toluene, pyridine, dischloroethane, trichloroethane, tetrahydrofuran and dimethyl sulfoxide, adding a small amount of an alkali, heating the mixture to precipitate the alkali salt of uroporphyrin III, and recovering the salt by filtration, for example. Or it is also possible to hydrolyze the ester with a mineral acid, neutralizing the hydrolyzation product with a suitable alkali, and recovering the precipitated alkali salt of uroporphyrin.

In the process of this invention, it is also possible to recover uroporphyrin III from the reaction product of microbial cells separated from the resulting culture broth, preferably microbial cells separated from the culture broth obtained by cultivating a uroporphyrin III-producing microorganism of the genus Arthrobacter in a culture medium under uroporphyrin III-producing conditions suitable for the growth of the microbial cells, or the crude enzyme extract thereof, with a uroporphyrin III-forming substrate. The uroporphyrin III-forming substrate may include glycine, fumaric acid, alpha-ketoglutaric acid, succinic acid, delta-aminolevulinic acid, salts of these acids, and substances containing these compounds. The salts of these acids may, for example, be sodium, potassium and ammonium salts of these acids. The aforesaid crude enzyme extraction can be performed by milling the microbial cells, breaking the microbial cells by ultrasonic treatment, breaking the microbial cells by utilizing an abrupt difference in pressure, or by breaking the microbial cells by using an enzyme having the ability to decompose cellular walls. Extraction can be performed in the same way as in the extraction of uroporphyrin III from the culture broth as described hereinabove.

The above reaction can be performed at a temperature of about 20° C. to about 40° C. and at a pH of about 4 to about 9.5 for a period of about 5 hours to about 5 days. In performing the reaction, the reaction system may be kept stationary, or placed under shaking or agitation. Uroporphyrin III can be separated and recovered from the reaction product in the same way as in the recovery of uroporphyrin III from the culture broth as described hereinabove.

In this manner, uroporphyrin III can be obtained in high yields from the culture broth either directly or indirectly through a further reaction.

Uroporphyrin III obtained by the process of this invention can be easily converted to uroporphynogen III by treatment with NaHg, for example. The uroporphynogen III can be converted to vitamin $B_{12}$ through Cobyrinic acid, as described in Bioorg. Chem., 6, 397, (1977), or J. Am. Chem. Soc., 94, 8269, (1972). Furthermore, it is also useful as medicines, synthetic intermediates therefor, and red dyes for foods and drinks.

The following Examples further illustrate the process of this invention specifically.

Uroporphyrin III in the culture broth was determined in the following manner.

Ethyl acetate (10 ml) was added to 1 ml of the culture broth or its diluted product and 10 ml of 1/10 N acetate buffer to perform extraction. Coproporphyrin III included as an impurity moved to the ethyl acetate layer. The ethyl acetate layer was washed with water, and combined with the aqueous layer. The mixture was extracted with 20 ml of a mixture of ethyl acetate and acetic acid in a ratio of 3:1. The ethyl acetate layer was extracted with 10 ml of 5% hydrochloric acid, and the hydrochloric acid layer was analyzed by a spectrophotometer. After confirming that the maximum absorption wavelength was 405.5 m$\mu$, the concentration of uroporphyrin III was calculated using a separately prepared calibration curve.

EXAMPLE 1

*Arthrobacter hyalinus* (FERM-P No. 3125; ATCC 31263) was inoculated in a 500 ml. Erlenmeyer flask containing 200 ml of a sterilized culture medium containing, per liter of deionized pure water, 10 g of glucose, 1.0 g of yeast extract, 3.0 g of peptone, 3.0 g of ammonium nitrate, 0.4 g of monopotassium phosphate, 1.5 g of disodium phosphate, 5.0 g of magnesium sulfate, 10 mg of manganese sulfate, 10 mg of zinc sulfate, 200 $\mu$g of copper sulfate, 10 $\mu$g of molybdenum and 5.0 g of calcium carbonate, and cultivated at 30° for 3 days under shaking. Thereafter, a 50% aqueous solution of glucose was added every 2 to 3 days, and during a cultivation period of 17 days, 80 g of glucose per liter of the culture broth was added.

The concentration of uroporphyrin III accumulated in the culture broth was 89 mg/liter.

EXAMPLE 2

Four liters of the culture broth contained in 20 Erlenmeyer flasks (500 ml.) which was obtained by the same cultivation procedure as in Example 1 was centrifuged at 10,000 G for 10 minutes. The resulting supernatant liquid was adjusted to pH 2.6, and centrifuged at 1,000 G for 10 minutes in order to collect the precipitate. Methanol and hydrochloric acid were added to the precipitate, and the mixture was allowed to stand at room temperature for 30 minutes, followed by extraction with dichloromethane. The dichloromethane layer was repeatedly washed with water until hydrochloric acid was removed from it. The dichloromethane layer was concentrated, and purified by silica gel chromatography to afford 280 mg of an octamethyl ester of uroporphyrin III as crystals.

Figure 2:
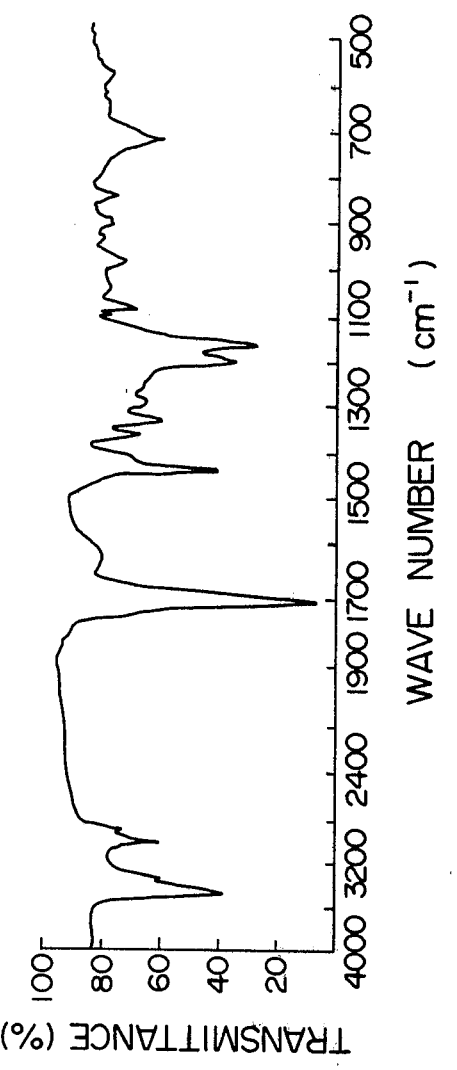

The absorption spectrum in the visible region of the resulting ester was as shown in FIG. 1 which shows an absorption maximum at 405.5, 501, 535, 571, and 626 m$\mu$. The infrared absorption spectrum of the ester was as shown in FIG. 2 which shows an absorption maximum at 3430, 2950, 1730, 1440, 1365, 1330, 1200, 1170, 1090, and 1000 cm$^{-1}$.

Figure 3:
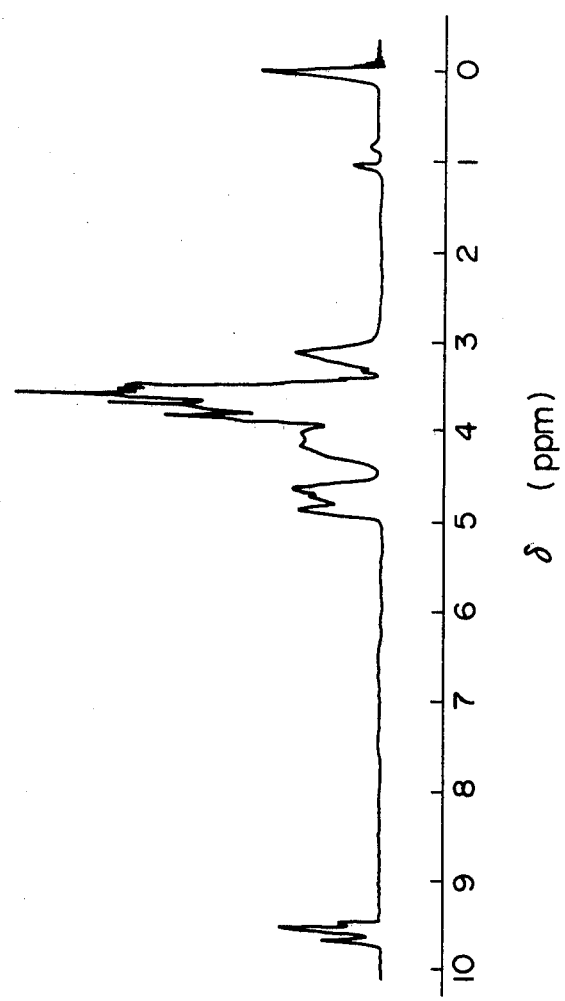

The results of nuclear magnetic resonance spectroscopy of the product in deuterochloroform were as shown in FIG. 3.

The product had a melting point of 256° to 259° C., which corresponded to the value shown in the literature, J. of Biol. Chem., 157, 323, (1945).

From the above data, the product was identified as uroporphyrin III.

Example 3

Uroporphyrin III, octamethyl ester, (200 mg) obtained in Example 2 was dissolved in 4 ml of toluene, and an aqueous solution of sodium hydroxide was added. The solution was heated at 95° C. for 30 minutes. After the reaction, the reaction mixture was filtered, and the precipitate was collected from the filtrate to obtain 200 mg of uroporphyrin III, octasodium salt. Its purity, determined by a colorimetric method, was 99%.

EXAMPLE 4

Cultivation was performed for 17 days in the same way as in Example 1 except that *Arthrobacter pascens* IFO 12139 was used. The concentration of uroporphyrin III accumulated in the resulting culture broth was 38 mg/liter.

EXAMPLE 5

*Arthrobacter hyalinus* (FERM-P No. 3125; ATCC 31263) was inoculated into a test tube having an outside diameter of 21 mm and containing 15 ml of a sterilized culture medium containing, per liter of deionized pure water, 10 ml of isopropyl alcohol, 1.0 g of yeast extract, 3.0 g of peptone, 3.0 g of ammonium nitrate, 0.4 g of monopotassium phosphate, 1.5 g of disodium phosphate, 5.0 g of magnesium sulfate, 10 mg of manganese sulfate, 10 mg of zinc sulfate, 200 $\mu$g of copper sulfate, 10 $\mu$g of molybdenum trioxide and 5.0 g of calcium carbonate, and cultivated at 30° C. for 3 days under shaking. Isopropyl alcohol was added every 2 to 3 days thereafter, and during a cultivation period of 17 days, 85 ml of isopropyl alcohol was added per liter of the culture broth.

The concentration of uroporphyrin III accumulated in the culture broth was 64 mg/liter.

EXAMPLE 6

Cultivation was carried out for 17 days in the same way as in Example 5 except that 0.2 g of L-cystine was further added per liter of deionized pure water to the culture medium.

The concentration of uroporphyrin III accumulated in the culture broth was 101 mg/liter.

EXAMPLE 7

Cultivation was carried out for 17 days in the same way as in Example 6 except that 5-methyl-DL-tryptophan-resistant NOC strain NOC11001 (FERM-P No. 5256) of *Arthrobacter hyalinus* was used instead of the *Arthrobacter hyalinus* (FERM-P No. 3125).

The concentration of uroporphyrin III accumulated in the culture broth was 260 mg/liter.

EXAMPLE 8

Cultivation was carried out for 17 days in the same way as in Example 6 except that coproporphyrin III-resistant strain (FERM-P No. 5259) of *Arthrobacter hyalinus* was used instead of *Arthrobacter hyalinus* (FERM-P No. 3125).

The concentration of uroporphyrin III accumulated in the culture broth was 470 mg/liter.

EXAMPLE 9

Cultivation was carried out for 17 days in the same way as in Example 4 except that 0.2 g of L-cystine was further added per liter of deionized pure water to the culture medium.

The concentration of uroporphyrin III accumulated in the culture broth was 44 mg/liter.

EXAMPLE 10

Cultivation was performed for 17 days in the same way as in Example 9 except that L-tryptophan-resistant strain NOC11003 (FERM-P. No. 5257) of *Arthrobacter pasencs* was used instead of *Arthrobacter pascens* (IFO 12139).

The concentration of uroporphyrin III accumulated in the culture broth was 72 mg/liter.

EXAMPLE 11

Production of strain FERM-P No. 5256:

*Arthrobacter hyalinus* FERM-P No. 3125 was inoculated into a test tube having an outside diameter of 21 mm and containing 15 ml of the sterilized culture medium (referred to as a P medium) shown in Example 5, and cultivated at 30° C. for 3 days under shaking. The culture broth was put into a Petri dish, and subjected to ultraviolet radiation (two 15 W lamps located 40 cm above the Petri dish) for 2 minutes. The treated culture broth was inoculated into 15 ml of the sterilized P medium containing 5-methyl-DL-tryptophan in a test tube having an outside diameter of 21 mm and the mixture was cultivated for 10 days in a test tube. The resulting culture broth was inoculated into a plate containing the P medium containing 5-methyl-DL-tryptophan and agar, and cultivated at 30° C. Among the resulting colonies, that which had the high activity to produce uroporphyrin III was separated as a 5-methyl-DL-tryptophan-resistant strain of *Arthrobacter hyalinus*.

EXAMPLE 12

Production of FERM-P No. 5259 strain:

Cultivation was carried out in the same way as in Example 1 except that coproporphyrin III was added to the culture medium instead of 5-methyl-DL-tryptophan. Among the resulting colonies, that which showed a high ability to produce uroporphyrin III was separated as a coproporphyrin III-resistant strain of *Arthrobacter hyalinus*.

EXAMPLE 13

Production of FERM-P No. 5257 strain:

*Arthrobacter pascens* (IFO 12139) was inoculated into a test tube having an outside diameter of 21 mm and containing 15 ml of the sterilized culture medium (to be referred to as a G medium) shown in Example 1, and cultivated for 3 days at 30° C. under shaking. The culture broth was put into a Petri dish, and subjected to ultraviolet radiation for 2 minutes using two 15 W lamps located 40 cm above the Petri dish. The treated culture broth was inoculated into 15 ml of the sterilized G medium containing L-tryptophan in a test tube having an outside diameter of 21 mm and the mixture was cultivated for 10 days in the tube. The culture broth obtained was inoculated into a plate having the G medium containing L-tryptophan and agar. Among the resulting colonies, that which had the high ability to produce uroporphyrin III was separated as an L-tryptophan-resistant strain of *Arthrobacter pascens*.

What we claim is:

1. A process for producing uroporphyrin III, which comprises cultivating a uroporphyrin III-producing microorganism of *Arthrobacter hyalinus, Arthrobacter pascens* or a variety or mutant thereof in a culture medium containing a carbon source, a nitrogen source and a mineral, and recovering uroporphyrin III from the culture broth.

2. The process of claim 1 wherein the cultivation is carried out at a temperature of about 20° to about 40° C. and a pH of about 4 to about 9.5.

3. The process of claim 1 wherein the culture medium contains at least one component selected from L-cystine and $Mg^{++}$.

4. The process of claim 3 wherein the amount of L-cystine is about 0.1 g to about 5 g per liter of the culture medium.

5. The process of claim 3 wherein the amount of $Mg^{++}$ is about 0.5 g to about 10 g per liter of the culture medium.

6. The process of claim 1 which comprises reacting the microbial cells separated from the culture broth or the crude enzyme extract of the microbial cells with a uroporphyrin III-forming substrate, and recovering uroporphyrin III from the resulting reaction product.

7. The process of claim 1 wherein the uroporphyrin III-producing microorganism is *Arthrobacter hyalinus* FERM-P No. 3125 strain, *Arthrobacter hyalinus* ATCC 31263 strain, *Arthrobacter hyalinus* DSM 867 strain, *Arthrobacter pascens* IFO 12139 strain, *Arthrobacter pascens* ATCC 14358 strain, a 5-methyl-DL-tryptophan-resistant strain FERM-P No. 5256 of *Arthrobacter hyalinus*, a coproporphyrin III-resistant strain FERM-P No. 5259 of *Arthrobacter hyalinus*, or an L-tryptophan-resistant strain FERM-P No. 5257 of *Arthrobacter pascens*.

* * * * *